United States Patent
Dönig et al.

(10) Patent No.: US 6,743,201 B1
(45) Date of Patent: Jun. 1, 2004

(54) CASSETTE FOR DELIVERING FLUIDS, ESPECIALLY DIALYSIS FLUIDS

(75) Inventors: Rainer Dönig, Frankfurt (DE); Wolfgang Schulz, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/285,120

(22) Filed: Apr. 1, 1999

(30) Foreign Application Priority Data

Apr. 1, 1998 (DE) .......................................... 198 14 695

(51) Int. Cl.$^7$ .......................... A61M 5/00; A61M 1/00; C02F 9/00; F28F 3/12
(52) U.S. Cl. ........................ 604/114; 604/153; 210/252; 210/257.1; 210/258; 165/169; 165/170
(58) Field of Search ............................... 604/4.01, 6.11, 604/6.13, 152, 153, 5.01–5.04, 6.09, 6.1, 28–29, 113–14, 131, 141; 422/46, 44; 210/258, 252, 321, 64, 175, 321.72, 181–183, 645–46, 650, 255–56, 257.1, 259–61, 176–78; 607/96, 104–105, 113–114; 392/311, 465, 472, 473, 479–83, 485–89; 219/385–86, 520–21, 524–25, 528; 165/58, 61, 64, 46, 168–84; 137/334–341

(56) References Cited

U.S. PATENT DOCUMENTS

| | | | |
|---|---|---|---|
| 4,532,414 A | * | 7/1985 | Shah et al. ................. 392/470 |
| 5,245,693 A | * | 9/1993 | Ford et al. ................. 392/470 |
| 5,381,510 A | * | 1/1995 | Ford et al. |
| 5,542,919 A | | 8/1996 | Simon et al. |
| 5,628,908 A | * | 5/1997 | Kamen et al. ............... 210/646 |

FOREIGN PATENT DOCUMENTS

| EP | 0 482 858 | 4/1992 |
|---|---|---|
| EP | 0 687 474 | 12/1995 |

* cited by examiner

Primary Examiner—Patricia M. Bianco
(74) Attorney, Agent, or Firm—Kenyon & Kenyon

(57) ABSTRACT

A cassette for delivering fluids, especially dialysis fluids, with connecting elements for connecting solution bags and lines leading to the patient for to the dialysis machine, with at least one delivery chamber with an inlet and outlet, with lines for carrying the fluids supplied and delivered, with the walls of the lines being designed at least in some sections so that the lines can be closed by applying a compressive force acting on the walls. Heating and delivery of fluids, in particular dialysis fluids, can be performed effectively and simply by providing at least one area in the cassette where the lines are arranged in such a way that the medium in the lines can be heated to a predetermined set point by means of a heating device arranged outside the cassette. A dialysis machine, in particular for carrying out peritoneal dialysis, hemofiltration and plasma filtration, with a recess or device to accommodate a cassette according to the present invention and with a pump unit for operating the delivery chambers of the cassette. A heating device is provided in the dialysis machine, arranged in the area of the recesses or devices to accommodate the cassette. A method of delivering, balancing, metering and heating a medical fluid, where a fluid conveyed through the lines or at least one delivery chamber is also exposed to heating energy at the same time.

13 Claims, 1 Drawing Sheet

CASSETTE FOR DELIVERING FLUIDS, ESPECIALLY DIALYSIS FLUIDS

FIELD OF THE INVENTION

The present invention relates to a cassette for delivering fluids, in particular dialysis fluids. The present invention also concerns a dialysis machine in which a cassette for delivering fluids, in particular dialysis fluids, can be accommodated and a method of delivering a medical fluid.

BACKGROUND OF THE INVENTION

Generic cassettes for delivering fluids, in particular dialysis fluids, are known from International Patent WO 97/09,074 and are usually used as exchange items in dialysis machines. Such cassettes can fulfill the function of delivery of dialysis fluid with separation of media. A delivery chamber arranged in the cassette is driven pneumatically by a corresponding drive unit of the dialysis machine. It is also possible to use mechanically or hydraulically operated delivery chambers. The delivery chamber has a membrane that is activated by the drive unit and ensures that a separation between the media to be delivered and the working medium of the dialysis machine is guaranteed. The fluid flow in the cassette is controlled by means of pneumatically operated valves. To heat the dialysis fluid to be administered to the patient to the desired temperature level and keep it at that level, International Patent WO 97/09074 discloses trays on which the solution bags are stored during dialysis. For example, the trays are heated by heating cartridges which are in turn driven by a control unit of the dialysis machine.

With such an arrangement, it is a disadvantage that the heating of the dialysis fluids is uneven due to the one-sided storage on the heating trays and is associated with considerable heat loss. Furthermore, a separate heating step is necessary, which accordingly makes the design of the dialysis machine costly.

OBJECT OF THE INVENTION

An object of the present invention is to create a device by which fluids, in particular dialysis fluids, can be easily and effectively heated and delivered.

This and other objects are achieved with a generic cassette having at least one area where fluid lines are arranged such that the medium in the lines can be heated to a predetermined set point by a heating device arranged outside the cassette. Cassettes according to the present invention have the advantages that the partial functions of delivering, metering/balancing, mixing, measuring, connecting and heating of medical fluids can be combined and performed in one unit. This greatly facilitates operation of the system and makes it more fail-safe by minimizing the steps that are subject to risk. The fact that the cassette according to the present invention is consistently connected in such a way that the media are separated permits sterile processing and thus reliably guards against the risk of infection.

According to a preferred embodiment of the present invention, a cassette includes a base structure with one or more films which cover at least part of the base structure and which are connected to the base structure. Walls of lines and a delivery chamber are formed by the base structure and the films. In the area of delivery chambers, the film is designed to be suitably elastic to serve as a membrane which is moved by the drive unit, e.g., by a piston pump, in accordance with a desired delivery height in the delivery chamber. The lines of the cassette which serve to guide the fluid flow are also bordered by the base structure and the film covering it. It is thus possible for only one wall of the lines or multiple walls to be formed by films.

In another embodiment of the present invention, a film extends on both sides of the base structure. This is advantageous especially in the area of the cassette, in that the lines are arranged in such a way that the medium in the lines can be heated to a predetermined set point by a heating device outside the cassette. In this case it is possible, with both sides of the film being used, to effectively heat both sides of the cassette and thus also the media flow, which is guided accordingly.

It is especially advantageous if one side of the base structure is completely covered with a film. In this case, the film in the area of the delivery chambers serves as an elastic membrane which causes the dialysis fluid, for example, to be delivered, while also permitting separation of media. In the area of the lines, the film forms one of the walls and permits especially effective and advantageous heat transfer into the medium in the line. Manufacture of the cassette is also simplified in this case, because the base structure has only recesses or indentations to form the delivery chambers or lines and then is covered with a film according to the invention, so that the recesses become delivery chambers and the channels in the base structure become lines. The film can be applied to the base structure relatively easily by welding or gluing.

According to a preferred embodiment of the present invention, two delivery chambers are provided. It is thus possible to achieve a relatively uniform flow through the cassette as well as an attached dialysis machine or patient, respectively, with alternating operation of the delivery chambers through a suitably coordinated drive unit. With a corresponding separation of the delivery chambers, it is likewise possible for one of the delivery chambers to be provided for a high pressure range and another to be provided for a vacuum or low pressure range, for example. Both delivery chambers can be bordered by the base structure in the cassette and by the film applied to it. Control of the media flow through the cassette and corresponding control of the delivery chambers can be achieved by line walls which are designed to be closed by applying a compressive force thereto. This compressive force may be applied pneumatically or mechanically by valve tappets, for example.

In another embodiment of the present invention, the lines are arranged in a spiral, at least in the heatable area of the cassette. This affords the advantage that a relatively great line length is arranged on a relatively small area of the cassette, which permits especially effective heating of the media in the lines. In addition to a spiral arrangement, other configurations having a high ratio of line length to line area, just as on achieving a turbulent flow even at relatively low flow rates.

It is especially advantageous if areas with a spiral arrangement of lines extend on both sides of the base structure. This makes it possible to heat the fluid to be heated first on one side of the cassette with a suitably arranged heating device and to keep it at the desired temperature in passing the other side of the cassette or to heat it further as needed.

The areas on different sides of the base structure may be connected to a hole provided in the base structure. It is thus possible to direct the media first to one side of the base structure and heat them, and then to direct them to the other side through the hole and heat them further, which is especially effective when the lines on both sides are arranged in the form of a spiral.

According to a preferred embodiment of the present invention, the base structure is made at least partially of plastic, which advantageously can be produced by injection molding methods, for example, in a variety of designs.

It is especially advantageous to provide the base structure with holders for mounting transducers, for mounting pressure, temperature and/or flow rate sensors. For example, temperature sensors may detect the temperature of a dialysis solution through the film and transmit the values to an analyzer unit. To regulate a temperature set point, the fluid delivery rate can be varied through the heated solutions or the heating power can be changed at a constant fluid delivery rate.

According to a preferred embodiment of the present invention, a line leading to the patient and a drainage tube which are undetachably connected to the cassette are provided. Thus, the cassette can be manufactured with these lines, while the assignment of the other connection elements of the cassette can be selected and implemented by a machine operator in accordance with the required dialysis method.

The present invention also relates to a dialysis machine, in particular for performing peritoneal dialysis, hemodialysis and plasma filtration methods, with a recess or device to accommodate a cassette according to the present invention, as well as having a pump unit for operating a delivery chambers of the cassette. To heat the cassette according to this invention, a heating device can be provided and arranged in the area of the recess or device for accommodating the cassette. It is thus possible according to the invention to use a new cassette with each patient, with the cassette being inserted into the dialysis machine or suitably arranged on it. Connecting the cassette to the dialysis machine in such a manner that the media are separated permits sterile processing and ensures aseptic conditions even when the dialysis machine is used by multiple patients. The risk of infection is effectively minimized since the cassette is a disposable unit which need not be reused.

On the whole, the invention is a simple, reliable and effective dialysis system where a machine operator need only arrange a cassette in the recess or device provided for it or connect the required lines after entering the desired set points. No separate arrangement of heating devices or elements is necessary.

In another embodiment of the present invention, the heating device has sheet or panel-type heating elements. This is especially advantageous in embodiments where a cassette has planar areas containing lines arranged in the form of a spiral, for example. In this case, especially effective heating of the media flowing through the lines is possible.

The heating device may extend to both sides of the recess or device for accommodating the cassette in such a way that the cassette can be heated on both sides. While requiring relatively little space, this embodiment case affords effective heating of the media to a desired set point even at high fluid rates.

The present invention also relates to a method for delivering, balancing, metering and heating a medical fluid, where a fluid delivered through lines and at least one delivery chamber is simultaneously receiving heat energy. This yields a method that is simple to carry out, where the partial functions of, for example, delivering, metering/balancing, mixing, measuring, connecting and heating medical fluids can be combined or performed in a compact manner.

It is especially advantageous if fluid is first sent through the delivery chambers and then heated in an area encompassing the lines. However, heating also may take place in the delivery chambers, alone or in combination with heating in the lines. Heating the fluid in the lines has the advantage that a great length of line can be accommodated as a result of the favorable arrangement of the lines in a relatively small area. This affords the possibility of heating the fluid effectively and in a controlled manner even at high flow rates.

Heating may take place in an area where the lines are arranged in spiral form. This yields an especially advantageous ratio of line length per unit of area, permitting especially effective heating.

In another embodiment of this invention, fluid first is passed through at least one delivery chamber of a cassette provided for delivering, balancing, metering and heating of fluid and is heated in lines on one side of the cassette, after which the fluid is transferred to the opposite side of the cassette and is heated further in lines on the opposite side. With such an arrangement, the fluid can be heated adequately even at high flow rates due to the relatively great line length extending on both sides of the cassette.

Additional advantages and details of the present invention are explained below on the basis of the embodiments described and illustrated in the figure.

DETAILED DESCRIPTION OF THE PREFERRED EMBODIMENT

Figure 1:
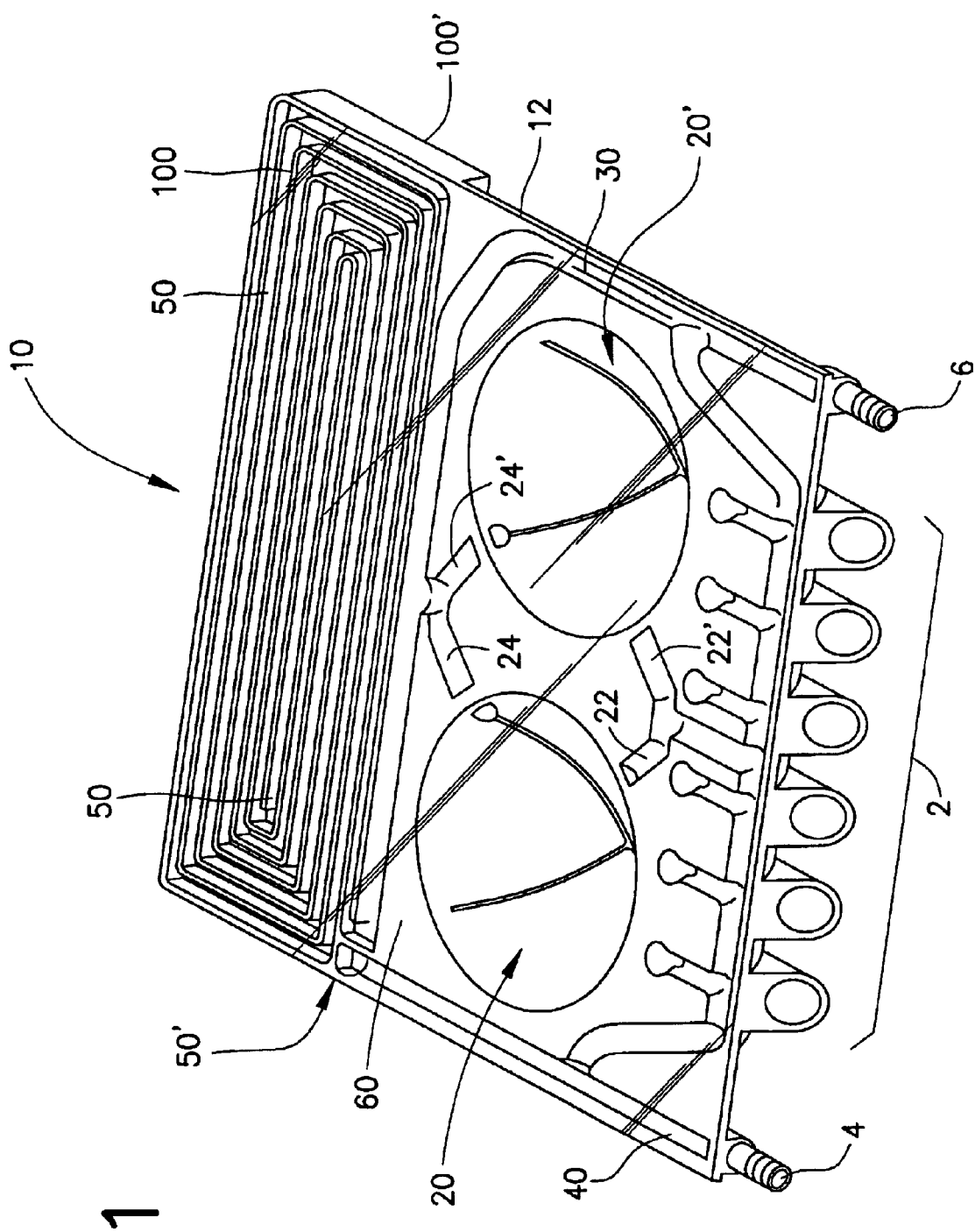
FIG. 1 is a perspective view of a cassette according to the invention with two delivery chambers and with areas for heating the fluids being delivered.

FIG. 1 shows a cassette 10 according to the invention which is designed as a disposable unit and which can be inserted into a suitably designed recess or receptacle of a dialysis machine. Reference numbers 2, 4, 6 indicate connecting elements for connecting solution bags, lines leading to the patient or to a dialysis machine and/or drainage lines. Two permanently attached hose lines can be arranged on connections 4 and 6, one connection being the patient hose line and the other being the drainage hose line. Connecting elements 2 serve to connect solution bags or other medication containers, for example.

Cassette 10 includes a base structure 12 which preferably is made of plastic and can be manufactured by an injection molding or deep-drawing technique. Recesses and channels run in base structure 12, some forming the walls of the two adjacent delivery chambers 20, 20' and the lines 30, 40, 50, 50' arranged in the cassette. The lines leading from connecting elements 2 and inlets 22, 22' and outlets 24, 24' of delivery chambers 20, 20' are formed in part by base structure 12.

A film 60 is welded to base structure 12 and is provided over the entire surface of the side of base structure 12 shown at the top of FIG. 1. Film 60 forms the borders of the channels and recesses formed in base structure 12, thus bordering, for example, lines 30, 40, 50, 50' and delivery chambers 20, 20'. Inlets 22, 22' and outlets 24, 24' of delivery chambers 20, 20' are bordered by film 60 on one side.

In the areas 100, 100' arranged above delivery chambers 20, 20' as shown in FIG. 1, lines 50, 50' are arranged so that the medium in lines 50, 50' can be heated to a predetermined set point by a heating device arranged outside the cassette 10. Lines 50, 50' extend on the top side (lines 50) and on the bottom side (lines 50') shown in FIG. 1.

The media supplied and delivered are controlled by the fact that the walls of lines 30, 40, 50, 50' and the walls of inlet 22, 22' and outlet 24, 24' of the delivery chambers 20, 20' can be closed by applying a compressive force to the walls. This compressive force may be applied pneumatically, hydraulically or mechanically by valve tappets, which can be controlled by a control unit of a dialysis machine.

Solution bags and other medication containers can be connected by means of connecting elements 2, which are shown in FIG. 1, and also have contact protection. The media supplied are introduced into delivery chambers 20 or 20' at appropriate valve settings by means of inlets 22, 22', and can be pumped out of delivery chambers 20, 20' by the movement of film 60, such as can be induced by a drive unit of a dialysis machine. This is effected by means of outlets 24, 24' which come together and open into a first section of line 50. The medium conveyed then flows through line 50, which is now on the top side in area 100, and is heated by a heating device of the dialysis machine arranged accordingly. In the end area of line 50 which is arranged in spiral form, a hole forms a fluid connection to the area 100' of base structure 12 on the bottom side. Accordingly, the medium flows through the hole to the other side of base structure 12 into the line 50' which is also arranged in spiral form, and the fluid can again be heated. Then, the heated fluid exits the cassette 10 through connector 4 or the hose line connected to it and is provided to the patient or to the dialysis machine.

The cassette and the dialysis machine according to the present invention are suitable for use in peritoneal dialysis and in hemofiltration and plasma filtration. Accordingly, it can be used with peritoneal systems and systems with extracorporeal blood circulation.

The geometry of the lines according to FIG. 1 permits simple control of the media by closing the lines by coupling with valve tappets, for example, thus permitting satisfactory function in both high and low pressure ranges. Areas 100, 100' can be heated accordingly on the front or back sides by means of sheet-type or panel heating elements (e.g., ohmic). The geometry of lines 50, 50' is optimized specifically for good heat transfer with low throttle losses at the same time. Despite the high power density per unit of area (e.g., approximately 5 $W/cm^2$), the surface temperatures of the heating elements remain low (<100 degrees C.). This minimizes requirements regarding the thermal stability of film 60 and base structure 12.

Lines 40 and 30 can be used, for example, for fresh dialysis solutions or for spent dialysate in automatic peritoneal dialysis.

Due to the combination of delivery properties with separation of media and the advantageous heating properties, the cassette and the dialysis machine according to the invention can be used to advantage in automatic peritoneal dialysis (APD) as well as in various hemofiltration and plasma filtration methods (universal HDF, CVVHF, CVVHDF, PF, etc.) and in adsorber applications in combination with extracorporeal blood circulation.

What is claimed is:

1. A cassette for delivering fluids, comprising:
   a) at least one inlet line for receiving fluids;
   b) an outlet line for providing fluid to a patient;
   c) a heating line for containing the fluids while the fluids are heated, the heating line in fluid connection with the outlet line;
   d) a delivery chamber having at least one chamber inlet in fluid connection with the at least one inlet line and a chamber outlet connected to the heating line;
   e) a base structure forming the walls of the inlet line, outlet line, heating line, and forming a portion of the walls of the delivery chamber; and
   f) a film covering the delivery chamber and forming a remaining portion of the walls of the delivery chamber, wherein the film covering the delivery chamber is elastic and is constructed to be deflected by a pump;
   wherein the heating line is arranged such that a first segment of the heating line is exposed on one side of the cassette and a second segment of the heating line is exposed on the opposite side of the cassette so that the fluids within the heating line may be heated by a heating device located outside the cassette while the fluids are contained in the heating line.

2. The cassette of claim 1, wherein the delivery chamber is arranged within the cassette such that fluid within the chamber may be heated by a heating device located outside the cassette.

3. The cassette of claim 1, wherein the heating line is arranged in a spiral that allows heating of the fluid within the heating line by a heating device located outside the cassette.

4. A cassette for delivering fluids, comprising:
   a) at least two inlet lines for receiving fluid;
   b) an outlet line for providing fluid to a patient;
   c) a heating line for containing the fluids while the fluids are heated, the heating line in fluid connection with the outlet line;
   d) a first delivery chamber having at least one chamber inlet in fluid connection with at least one inlet line and a chamber outlet in fluid connection with the heating line;
   e) a second delivery chamber having at least one chamber inlet in fluid connection with at least one inlet line and a chamber outlet in fluid connection with the heating line;
   f) a base structure having channels forming a portion of the walls of the inlet line, outlet line, heating line, and recesses forming a portion of the walls of the first and second delivery chambers; and
   g) film covering both sides of the base structure and forming a remaining portion of the walls of the inlet line, the outlet line, the heating line, the first delivery chamber, and the second delivery chamber, wherein the remaining portion of the walls of the first delivery chamber and the second delivery chamber are elastic and constructed to be deflected by a pump;
   wherein the heating line is arranged such that the remaining portion of the walls of a first segment of the heating line is exposed on one side of the cassette and the remaining portion of the walls of a second segment of the heating line is exposed on the opposite side of the cassette so that the fluids within the heating line may be heated by a heating device located outside the cassette while the fluids are contained in the heating line.

5. The cassette of claim 4, wherein the remaining portion of the walls of the inlet, outlet, and heating lines are elastic and may be compressed with a compressive force, thereby allowing control of the flow of fluid within the cassette.

6. The cassette of claim 5, wherein the compressive force is pneumatic force.

7. The cassette of claim 5, wherein the compressive force is mechanical force.

8. The cassette of claim 4, wherein the pump is a piston pump.

9. The cassette of claim 4, wherein at least a portion of the heating line is arranged in a spiral.

10. The cassette of claim 4, wherein the base structure is formed of plastic.

11. The cassette of claim 4, wherein the base structure includes at least one holder for mounting a sensor.

12. The cassette of claim 11, wherein the base structure is provided with at least one sensor selected from the group consisting of pressure sensors, temperature sensors, and flow rate sensors.

13. The cassette of claim 4, wherein the first and second segments of the heating line are in fluid communication.

* * * * *